(12) United States Patent
Ueno

(10) Patent No.: US 10,561,649 B2
(45) Date of Patent: Feb. 18, 2020

(54) PHARMACEUTICAL COMBINATION OF OPIOID AND PROSTAGLANDIN COMPOUND

(71) Applicant: SUCAMPO AG, Zug (CH)

(72) Inventor: Ryuji Ueno, Easton, MD (US)

(73) Assignee: SUCAMPO AG, Zug (CH)

( * ) Notice: Subject to any disclaimer, the term of this patent is extended or adjusted under 35 U.S.C. 154(b) by 0 days.

(21) Appl. No.: 15/805,759

(22) Filed: Nov. 7, 2017

(65) Prior Publication Data
US 2018/0311233 A1 Nov. 1, 2018

Related U.S. Application Data

(63) Continuation of application No. 12/166,834, filed on Jul. 2, 2008, now abandoned.

(60) Provisional application No. 60/929,556, filed on Jul. 3, 2007.

(51) Int. Cl.
A61K 31/485 (2006.01)
A61K 31/5575 (2006.01)
A61K 45/06 (2006.01)

(52) U.S. Cl.
CPC ........ *A61K 31/485* (2013.01); *A61K 31/5575* (2013.01); *A61K 45/06* (2013.01)

(58) Field of Classification Search
CPC ... A61K 31/485; A61K 31/5575; A61K 45/06
See application file for complete search history.

(56) References Cited

U.S. PATENT DOCUMENTS

| | | | |
|---|---|---|---|
| 4,158,062 A | 6/1979 | Canton et al. | |
| 4,569,937 A | 2/1986 | Baker et al. | |
| 5,166,174 A | 11/1992 | Ueno et al. | |
| 5,225,439 A | 7/1993 | Ueno et al. | |
| 5,284,858 A | 2/1994 | Ueno et al. | |
| 5,317,032 A | 5/1994 | Ueno et al. | |
| 5,380,709 A | 1/1995 | Ueno et al. | |
| 5,428,062 A | 6/1995 | Ueno et al. | |
| 5,886,034 A | 3/1999 | Ueno et al. | |
| 6,265,440 B1 | 7/2001 | Ueno et al. | |
| 6,414,016 B1 | 7/2002 | Ueno | |
| 6,982,283 B2 | 1/2006 | Ueno | |
| 7,064,148 B2 | 6/2006 | Ueno et al. | |
| 2003/0073746 A1 | 4/2003 | Ueno | |
| 2003/0119898 A1 | 6/2003 | Ueno et al. | |
| 2003/0166632 A1 | 9/2003 | Ueno | |
| 2004/0138308 A1 | 7/2004 | Ueno et al. | |
| 2006/0063830 A1 | 3/2006 | Ueno | |

FOREIGN PATENT DOCUMENTS

| | | | |
|---|---|---|---|
| FR | 2 392 005 A1 | 12/1978 | |
| FR | 2392005 A1 | 12/1978 | |
| JP | 2005-525405 A | 8/2005 | |
| WO | 2001/027099 A2 | 4/2001 | |
| WO | 02/089812 A1 | 11/2002 | |
| WO | 2002/089812 A1 | 11/2002 | |
| WO | 03/092648 A1 | 11/2003 | |
| WO | 2006/025599 A1 | 3/2006 | |
| WO | 2007/103540 A2 | 9/2007 | |
| WO | 2008/021394 A2 | 2/2008 | |

OTHER PUBLICATIONS

Ueno, Ryuji et al., "Effects of lubiprostone on morphine-induced constipation and analgesia", Gastroenterology, vol. 130, No. 4, Suppl. 2, Apr. 2006, pp. A373-A374 & Digestive Disease Week Meeting/107th Annual Meeting of the American-Gastroenterological-Association; Los Angeles, CA, USA; May 19 24, 2006.

Sorbera, L.A. et al., "Lubiprostone. Treatment of constipation, treatment of irritable bowel syndrome, treatment of postoperative ileus, ClC-2 channel activator", Drugs of the Future, Prous Science, ES vol. 29, No. 4, Apr. 1, 2004, pp. 336-341.

Rivkin, et al. "Lubiprostone: Chloride channel activator for chronic constipation", Clinical Therapeutics, Excerpta Medica, Princeton, NJ, US, vol. 28, No. 12, Jan. 12, 2007, pp. 2008-2021.

Wiinpenny, J P, "Lubiprostone Sucampo Pharmaceuticals/Takeda Pharmaceutical", IDRUGS, Current Drugs L to, GB, vol. 8, No. 5, May 1, 2005, pp. 416-422.

Christmas, A J, "The mouse anti-morphine constipation test—a simple laboratory test of the gastrointestinal side-effect potential of orally administered prostaglandin analogues", Prostaglandins, Butterworth, Stoneham, MA, US, vol. 18, No. 2, Aug. 1, 1979, pp. 279-284.

Dajani, E.Z., et al., "Effects of E Prostaglandins, Diphenoxylate and Morphine on Intestinal Motility In Vivo", European Journal of Pharmacology, Elsevier BV, NL, vol. 34, No. 1, Nov. 1, 1975, pp. 105-113.

Grunkemeier et al., "The Narcotic Bowel Syndrome: Clinical Features, Pathophysiology, and Management", Clinical Gastroenterology and Hepatology, American Gastroenterological Association, US, vol. 5, No. 10, Oct. 1, 2007, pp. 1126-1139.

(Continued)

*Primary Examiner* — Samira J Jean-Louis

(57) ABSTRACT

Provided is a method for treating a condition or disease which is one of the indications for opioid use, which comprises administering a combination of:

(a) a pharmaceutically effective amount of an opioid, and (b) a pharmaceutically effective amount of a prostaglandin (PG) compound represented by the formula (I):

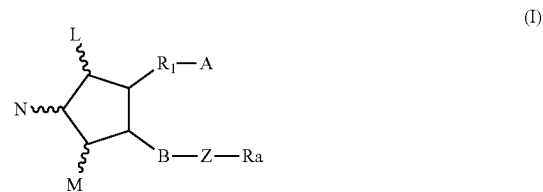

to a patient in need thereof.

7 Claims, No Drawings

(56) References Cited

OTHER PUBLICATIONS

Sun, X. et al., "844 Lubiprostone Reverses the Inhibitory Action of Morphine on Mucosal Secretion in the Human Jejunum", Gastroenterology, Elsevier, Philadelphia, PA, vol. 134, No. 4, Apr. 1, 2008, p. A-122.

Schiller. L.R., "New and Emerging Treatment Options for Chronic Constipation" Reviews in Gastroenterological Disorders, Medreview, LLC, Mercer Island, WA, US, vol. 4, No. Suppl. 02, Jan. 1, 2004, pp. S43-S51.

Ballantyne, Jane. Pain Physician, May 2007, vol. 10, pp. 479-491.

Chinese Office Action corresponding to Chinese Patent Application No. 2008-80023276.4, dated Sep. 8, 2011.

Staats, Peter S. MD et al., "Incidence of Constipation Associated with Long-acting Opioid Therapy: A Comparative Study", Southern Medical Association 2004, vol. 97, Issue 2, pp. 129-134.

Cuppoletti, J. et al., "Methadone, but not Morphine, Inhibits Stimulated Chloride Currents in CLC-2 Transfected Cells in Culture", Digestive Disease Week, 2010.

Kalso, et al., "Oxycodone", Journal of Pain and Symptom Management, Elsevier, New York, NY, US, vol. 29, No. 5, May 1, 2005, pp. 47-56.

Maxwell, T. "Cancer Pain Management in the Elderly". Geriatric Nursing, Mosby-Year Book, St. Louis, MO, US, vol. 21, No. 3, May 1, 2000, pp. 158-163.

Meert, T. F. et al., A preclinical comparison between different opioids: antinociceptive versus adverse effects, Pharmacology Biochemistry and Behavior, Elsevier, U. S. vol. 80, No. 2, Feb. 1, 2005, pp. 309-326.

BR Office action dated Sep. 30, 2018 in related Application No. PI0812832-4, 3 pp.

Fickel, Opioid receptor expression in the rat gastrointestinal tract: a quantitative study with comparison to the brain, Molecular Brain Research, 1997, vol. 46, pp. 1-8.

Kalso, How different is oxycodone from morphine?, Pain, 2007, vol. 132, pp. 227-228.

Neilsen, Oxycodone and morphine have distinctly different pharmacological profiles: Radioligand binding and behavioural studies in two rat models of neuropathic pain, Pain 2007, vol. 132, pp. 289-300.

Office action dated Jun. 13, 2019 from related KR Application No. 102018-7008035, 4 pp.

Office action dated Mar. 12, 2019 from related Kr Application No. 102018-7008035, 3 pp.

Webster, Efficacy of Lubriprostone for the Treatment of Opioid-Induced Constipation, Analyzed by Opinoid Class, Pain Medicine, 2018, vol. 19, pp. 1195-1205.

PHARMACEUTICAL COMBINATION OF OPIOID AND PROSTAGLANDIN COMPOUND

CROSS REFERENCE TO RELATED APPLICATIONS

This application claims the benefit of U.S. Provisional Application No. U.S. 60/929,556 filed Jul. 3, 2007.

TECHNICAL FIELD

The present invention relates to a pharmaceutical combination comprising an opioid and a specific prostaglandin compound for the treatment of pain from various etiologies.

The endogenous opioid system is a major inhibitory system in the central nervous system and plays a pivotal role in the modulation of pain. Activation of opioid receptors results in analgesia and anti-hyperalgesia in experimental models and in the clinic. The use of opioids is affected by a number of known side-effects and disadvantages such as a decrease in attention and concentration due to sedation, constipation and respiratory depression after taking the drug as well as the risk of drug abuse and drug addiction. Morphine is a standard drug used for the treatment of moderate or heavy cancer pain, and oxycodone places a substituted drug of morphine. It is reported that oxycodone causes severer constipation than morphine.

Prostaglandins (hereinafter, referred to as PGs) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

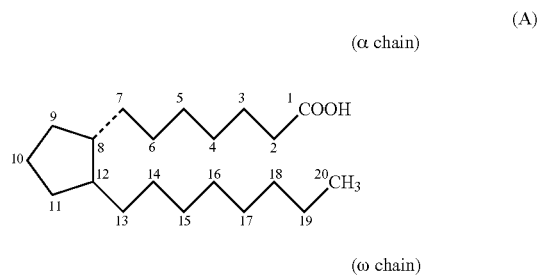 [SMILES: CCCCCCCCC1CCC[C@@H]1CCCCCCC(=O)O]

(A)

PGs are classified into several types according to the structure and substituents on the five-membered ring, for example, Prostaglandins of the A series (PGAs);

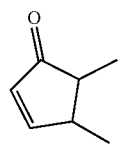

Prostaglandins of the B series (PGBs);

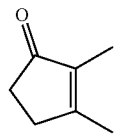

Prostaglandins of the C series (PGCs);

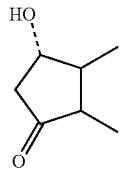

Prostaglandins of the D series (PGDs);

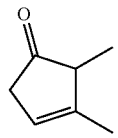

Prostaglandins of the E series (PGEs);

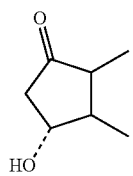

Prostaglandins of the F series (PGFs);

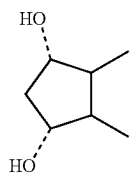

and the like. Further, they are classified into $PG_1$s containing a 13,14-double bond; $PG_2$s containing, 5,5- and 13,14-double bonds; and $PG_3$s containing 5,6-, 13,14- and 17,18-double bonds. PGs are known to have various pharmacological and physiological activities, for example, vasodilation, inducing of inflammation, platelet aggregation, stimulating uterine muscle, stimulating intestinal muscular activity, anti-ulcer effects and the like.

U.S. Pat. Nos. 5,225,439, 5,166,174, 5,284,858, 5,428,062, 5,380,709, 5,886,034 and 6,265,440 describe that certain prostaglandin E compounds are effective for the treatment of ulcers such as duodenal ulcer and gastric ulcer.

U.S. Pat. No. 5,317,032 to Ueno et al. describes prostaglandin analog cathartics, including the existence of bicyclic tautomers and U.S. Pat. No. 6,414,016 to Ueno describes the bicyclic tautomers as having pronounced activity as anti-constipation agents. The bicyclic tautomers, substituted by one or more halogen atoms can be employed in small doses for relieving constipation. At the C-16 position, especially, fluorine atoms, can be employed in small doses for relieving constipation.

U.S. Pat. No. 6,982,283 to Ueno et al. describes prostaglandin compound is useful for the treatment of drug-induced constipation.

U.S. Pat. No. 7,064,148 to Ueno et al. describes prostaglandin compound opens and activates chloride channels, especially ClC channels, more especially ClC-2 channel.

U.S. Patent publication No. 2003/0166632 to Ueno described ClC-2 channel opener is effective for the treatment of a disease or a condition responsive to opening of ClC-2 channel.

U.S. Patent publication No. 2003/0119898 to Ueno et al. describes specific composition of a halogenated prostaglandin analog for the treatment and prevention of constipation.

U.S. Patent publication No. 2004/0138308 to Ueno et al. describes chloride channel opener, especially a prostaglandin compound for the treatment of abdominal discomfort, and the treatment of functional gastrointestinal disorders such as irritable bowel syndrome and functional dyspepsia.

DISCLOSE OF THE INVENTION the present invention relates to a pharmaceutical combination comprising:
(a) an opioid and
(b) a prostaglandin (PG) compound represented by the formula (I):

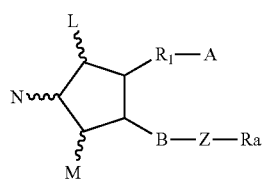

(I)

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —COOH or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is

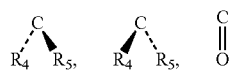

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxy, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, provided that Ra is substituted by halogen or Z is C=O.

By combining an opioid and a PG compound of formula (I), the effect of the opioid is augmented and/or the adverse side effect of the opioid such as constipation is well suppressed.

Especially, the present invention also relates to a pharmaceutical combination comprising:
(a) an oxycodone, and
(b) a prostaglandin (PG) compound represented by the formula (I).

In another aspect of the invention, there is provided a pharmaceutical composition comprising:
(a) a pharmaceutically effective amount of an opioid such as oxycodone, and
(b) a pharmaceutically effective amount of a prostaglandin (PG) compound represented by the formula (I) in association with a pharmaceutically suitable excipient.

According to the present invention, the composition comprising the two compounds may be formulate din a single dosage unit or separate dosage units.

Further more, the present invention provides a method for treating a condition of disease which is one of the indications for opioid use, which comprises administering a combination of:
(a) a pharmaceutically effective amount of an opioid such as oxycodone, and
(b) a pharmaceutically effective amount of a prostaglandin (PG) compound represented by the formula (I);
to a patient in need thereof.

According to the present invention, the (a) and (b) compounds may be administered simultaneously, separately or sequentially.

DETAILED DESCRIPTION OF THE INVENTION (a) Opioid

The term "opioid" as used herein refers to all drugs, both natural and synthetic, with morphine-like actions. An opioid suitable for the present invention is especially selected from the group comprising alfentanil, allylprodine, alphaprodine, anileridine, benzylmorphine, bezitramide, buprenorphine, butorphanol, clonitazene, codeine, cyclorphan, desomorphine, dextromoramide, dezocine, diampromide, dihydrocodeine, dihydromorphione, eptazocine, ethylmorphine, fentanyl, hydrocodone, hydromorphone, hydroxypethidine, levophenacylmorphan, levorphanol, lofentanil, methylmorphine, morphine, necomorphine, normethadone, normorphine, opium, oxycodone, oxymorphone, pholcodine, profadol sufentanil, pharmaceutically acceptable salts thereof, and mixtures thereof. The preferable example of opioid is oxycodone.

(b) The Compound of Formula (I)

The nomenclature of the prostaglandin compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in in the ω-chain, the number is deleted in the order staring from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-deoxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain ins extended by two carbon atoms, that is, having 9 carbon atoms in the α-chain is named as 2-decarboxy-2-(4-carboxybutyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluorotmethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A specific prostaglandin compound used in the present invention is represented by the formula (I):

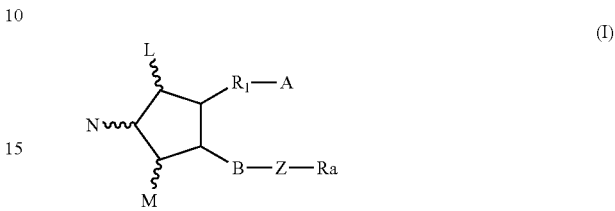

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is $-CH_3$, or $-CH_2OH$, $-COCH_2OH$, $-COOH$ or a functional derivative thereof;

B is single bond, $-CH_2-CH_2-$, $-CH=CH-$, $-C\equiv C-$, $-CH_2-CH_2-CH_2-$, $-CH=CH-CH_2-$, $-CH_2-CH=CH-$, $-C\equiv C-CH_2-$ or $-CH_2-C\equiv C-$;

Z is

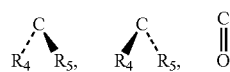

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower aryloxy; cyclo(lower)alkyl; cyclo(lower)alkyloxy; aryl; aryloxy; heterocyclic group; heterocyclic-oxy group, provided that Ra is substituted by halogen or Z is C=O.

A preferred compound used in the present invention is represented by the formula (II):

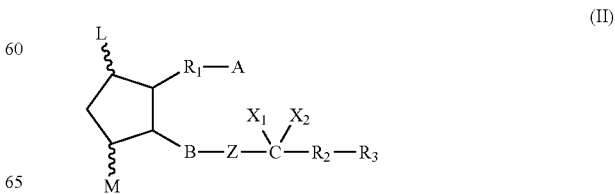

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, provided that one of X$_1$ and X$_2$ is substituted by halogen or Z is C=O.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 4 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isoproylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The terms "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidaxzolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl piperidino, piperazinyl, morpholino, indolyl, benzothienyl, quinolyl, isoquionolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), and alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethylmonoethanolamide salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of a mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolysulfonylamide.

Preferred examples of L an M include hydrogen, hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:

—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2CH_2$CH=CH—,
—$CH_2$—C≡C—$CH_2$—$CH_2$—$CH_2$—$CH_2$—$CH_2$, and
—$CH_2$—$CH_2$—$CH_2$—$CH_2$—$CH_2$—$CH_2$—CH($CH_3$)—$CH_2$—.

Preferred Ra is a hydrocarbon containing 1-20 carbon atoms, more preferably, 1-8 carbon atoms. Ra may have one or two side chains having one carbon atom.

Most preferred embodiment of the prostaglandin compound is 13,14-dihydro-15-keto-16,16-difluoro-prostaglandin $E_1$ compound or 13,14-dihydro-15-keto-16,16-difluoro-18-methyl-prostaglandin $E_1$ compound.

The configuration of the ring and the α- and/or ω chains in the above formulae (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto (=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds use din the invention include the bicyclic compound and analogs or derivatives thereof.

The bicyclic compound is represented by the formula (III):

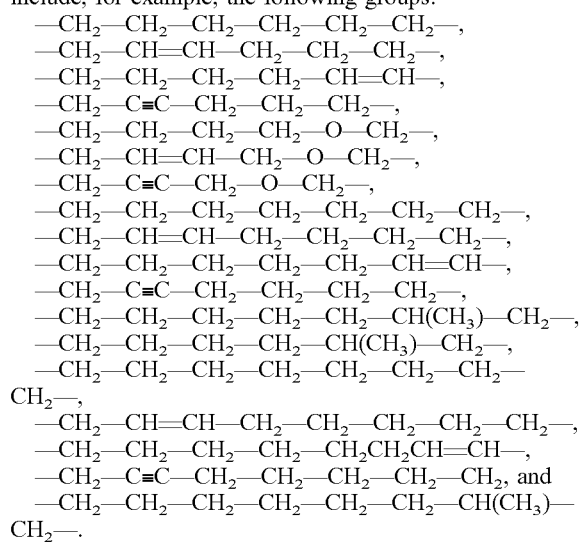

wherein, A is —$CH_3$, or —$CH_2OH$, —$COCH_2OH$, —COOH or a functional derivative thereof;

$X_1'$ and $X_2'$ are hydrogen, lower alkyl, or halogen;

Y is

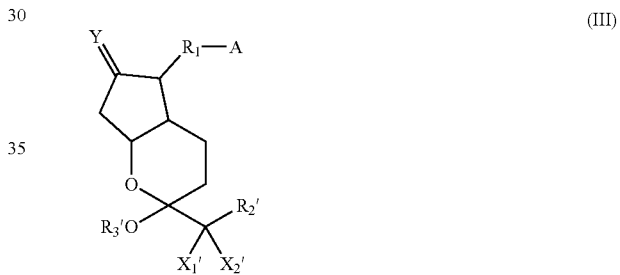

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)

alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other static isomers may be used in the same purpose.

The Pharmaceutically Suitable Excipient

According to the invention, the combination may be formulated in a pharmaceutical composition. The composition may be formulated as separate dosage forms each comprising individual active ingredient with a pharmaceutically suitable excipient, or as a single dosage form comprising two active ingredients with a pharmaceutically suitable excipient. The pharmaceutically suitable excipient may be, therefore, selected depending on the desired form of the composition According to the invention, "pharmaceutically suitable excipient" means an inert substance, which is suitable for the form, combined with the active ingredient of the invention.

For example, solid composition for oral administration of the present invention may include tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrate such as fibrous calcium gluconate; stabilizer such as cyclodextrin, for example, α,β- or γ-cyclodextrin; etherified cyclodextrin such as dimethyl-α-, dimethyl-β-, trimethyl-β-, or hydroxypropyl-β-cyclodextrin; branched cyclodextrin such as glucosyl-, maltosyl-cyclodextrin; formylated cyclodextrin, cyclodextrin containing sulfur, phospholipid and the like. When the above cyclodextrins are used, an inclusion compound with cyclodextrins may be sometimes formed to enhance stability. Alternatively, phospholipid may be sometimes used to form a liposome, resulting in enhanced stability.

Tablets or pills ma be coated with film soluble in the stomach or intestine such as sugar, gelatin, hydroxypropyl cellulose, or hydroxypropylmethyl cellulose phthalate as needed. Further, they may be formed as capsules with absorbable substances such as gelatins. Preferably, the composition is formulated in a soft gelatin capsule with liquid contents of the specific prostaglandin compound and a medium chain fatty acid triglyceride. Examples of the medium chain fatty acid triglyceride use din the present invention include a triglyceride of a saturated or unsaturated fatty acid having 6-14 carbon atoms which may have a branched chain. A preferred fatty acid is a straight chain saturated fatty acid, for example caproic acid (C6), caprylic acid (CB), capric acid (C10), lauric acid (C12) and myristic acid (C14). In addition, two or more medium chain fatty acid triglycerides may be use din combination. Further suitable excipients are disclosed in the published PCT application WO 01/27099.

A liquid composition for oral administration may be pharmaceutically acceptable emulsion, solution, suspension, syrup, or elixir, as well as generally used inactive diluent. Such composition may contain, in addition to the inactive diluent, adjuvants such as lubricants and suspensions, sweetening agents, flavoring agents, preservatives, solubilizers, anti-oxidants and the like. The details of the additives may be selected from those described in any general textbooks in the pharmaceutical field. Such liquid compositions may be directly enclosed in soft capsules. Solutions for parenteral administration, for example, suppository, enema and the like according to the present invention include sterile, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, fatty acid triglyceride, and vegetable oil such as olive oil, alcohols such as ethanol, polysorbate and the like. Such composition may contain adjuvants such as preservatives, wetting agent, emulsifier, dispersant, anti-oxidants and the like.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another form of the present invention is suppository or pessary, which may be prepared by mixing active ingredients into a conventional base such as cacao butter that softens at body temperature, and nonionic surfactants having suitable softening temperatures may be used to improve absorbability.

According to the method of the invention, the combination of the present invention can be administered systemically or locally by means of oral or parental administration, including a suppository, enema and the like. Single or multiple compositions may be administered to achieve the desired dose. According to the method, individual compounds in the combination may be administered simultaneously, separately, or sequentially.

According to the present invention, a mammalian subject may be treated by the instant invention by administering the compound used in the present invention. The mammalian subject may be any subject including a human. The compound may be applied systemically or topically. Usually, the compound may be administered by oral administration, intravenous injection (including infusion), subcutaneous injection, intra rectal administration, intra vaginal administration, transdermal administration and the like. The dose may vary depending on the strain of the animal, age, body weight, symptom to be treated, desired therapeutic effect, administration route, terms of treatment and the like. A satisfactory effect can be obtained by systemic administration 1-4 times per day or continuous administration at combination with the amount of 00001-0000 μg, more preferably 0.01-100000 μg, especially 0.1-1000 μg of specific prostaglandin compound, and 0.01-10000 mg, more preferably 0.1-1000 mg of Opioid at a daily dose.

The terms "combination" used herein means opioid and the specific prostaglandin compound, are both administered to a patient simultaneously in the form of a single entity or dosage, or are both administered to a patient as separate entities either simultaneously or sequentially with no specific time limits, wherein such administration provides therapeutically effective levels of the two components in the body, preferably at the same time.

The combination of the present invention is useful for the treatment of a disease or condition which is one of the indications for opioid use. For example, the combination is useful for the treatment or controlling pain from various etiology.

The terms "treatment" used herein includes any means of control such as prevention, care, relief of the condition, attenuation of the condition and arrest of progression.

The term "pain from various etiology" includes but is not limited to, inflammatory pain, hyperalgesia and, in particular, chronic pain, and means in particular pain consequential to trauma, e.g. associated with burns, sprains, fracture or the like, subsequent to surgical intervention, e.g. a post-operative analgesics, chemotherapy-inducted pain, as well as inflammatory pain of diverse genesis, e.g., bone and joint pain (osteoarthritis), myofascial pain (muscular injury, fibromyalgia), lower back pain, chronic inflammatory pain, chronic neuropathic pain, e.g., diabetic neuropathy, phantom limb pain and perioperative pain (general surgery, gynecologic surgery) as well as pain associated with, e.g., angina, menstruation or cancer.

The further details of the present invention will follow with reference to test examples, which, however, are not intended to limit the present invention.

Example

To examine the superior effect of combination of Compound 1 (13,14-dihydro-15-keto-16,16-difluoro-$PGE_1$) and oxycodone against the oxycodone-induced severe constipation, the severity of constipation was assessed using graphite marker propulsion ratio in the intestine as an index. Male Crlj: CD1 (ICR) mice were given oral administration of 0.1 mL of graphite maker (INK-30 containing 1% tragacanth gum). Immediately after administration of the graphite marker, the animals were treated orally with oxycodone at 5 mg/kg. The dosing volume of oxycodone was set at 5 mL/kg; the animals of the normal group were given the same volume of 0.5% CMC-Na. Immediately after administration of oxycodone or 0.5% CMC-Na, the animal was treated with Compound 1. The dosing volume of the Compound 1 was set at 5 mL/kg; the animals of the normal and control groups were given the same volume of water for injection. The animals were euthanized by cervical dislocation 150 minutes after administration of graphite marker, and the abdomen was cut open. The distance from the stomach to the cecum, and moving distance of the graphite marker in the intestine were measured. Propulsion rate was calculated by the following formula.

Propulsion rate (%)=(Moving distance of graphite marker/Distance from the stomach to the cecum)×100

In the normal group, the graphite marker propulsion ratio was 99.8±0.2%. In the control group, which had been treated with oxycodone at 5 mg/kg alone, the graphite marker propulsion rate was 62.3±5.6%. Compared with the normal group, the graphite marker propulsion ratio was significantly lower in the control group; indicating that oxycodone at 5 mg/kg significantly decreased propulsion of the graphite marker in the intestines. In the group treated with Compound 1 at 100 μg/kg and oxycodone at 5 mg/kg, the graphite marker propulsion ratio was 80.5±5.5%; compared with the control group, constipation was significantly improve dint his group.

The results indicate the beneficial effect of the combined administration of oxycodone and Compound 1.

TABLE 1

Effect of combined administration of Compound 1 and oxycodone on oxycodone-induced constipation in mice

| Test Group | n | Dosage of Compound 1 μg/kg | Dosage of Oxycodone mg/kg | The graphite marker propulsion rate Mean ± S.E., % |
|---|---|---|---|---|
| Normal | 15 | — | 0 | 99.8 ± 0.2 |
| Control | 15 | — | 5 | 62.3 ± 5.6[##] |
| Compound 1 | 15 | 100 | 5 | 80.5 ± 5.5* |

[##]p < 0.01 compared to normal group,
*p < 0.05 compared to control group.

What is claimed is:

1. A method for relieving a condition or disease which is one of the indications for opioid use, which comprises administering a combination of:
    (a) a pharmaceutically effective amount of oxycodone, a pharmaceutically acceptable salt thereof, or a mixture thereof, and
    (b) a pharmaceutically effective amount of 13,14-dihydro-15-keto-16,16-difluoro-prostaglandin $E_1$ to a subject in need thereof.

2. The method as described in claim 1, wherein the compounds are administered orally.

3. The method as described in claim 1 wherein the respective compounds are administered simultaneously, separately or sequentially.

4. The method as described in claim 1, wherein the disease or condition is pain.

5. The method as described in claim 4, wherein the pain is chronic pain.

6. The method as described in claim 1, wherein oxycodone is administered an amount from about 0.01 mg to about 10000 mg and 13,14-dihydro-15-keto-16,16-difluoro-prostaglandin $E_1$ is administered an amount from about 0.01 μg to about 10000 μg.

7. The method as described in claim 6, wherein the amount of oxycodone from about 0.1 mg to about 1000 mg and the amount of 13,14-dihydro-15-keto-16,16-difluoro-prostaglandin $E_1$ is from about 0.1 μg to about 1000 μg.

* * * * *